(12) United States Patent
Oglaza et al.

(10) Patent No.: US 10,383,672 B2
(45) Date of Patent: *Aug. 20, 2019

(54) UNIVERSAL ANCHOR FOR BONE FIXATION

(71) Applicant: Vexim S.A., Balma (FR)

(72) Inventors: Jean-Francois Oglaza, Balma (FR); Ezzine Banouskou, Tournefeuille (FR)

(73) Assignee: VEXIM S.A., Balma (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,302

(22) Filed: Oct. 30, 2017

(65) Prior Publication Data

US 2018/0071002 A1 Mar. 15, 2018

Related U.S. Application Data

(63) Continuation of application No. 14/385,125, filed as application No. PCT/EP2013/055015 on Mar. 12, 2013, now Pat. No. 9,801,674.

(60) Provisional application No. 61/609,728, filed on Mar. 12, 2012.

(51) Int. Cl.
| | | |
|---|---|---|
| *A61B 17/88* | (2006.01) | |
| *A61B 17/68* | (2006.01) | |
| *A61B 17/70* | (2006.01) | |
| *A61B 17/86* | (2006.01) | |

(52) U.S. Cl.
CPC ............ *A61B 17/88* (2013.01); *A61B 17/686* (2013.01); *A61B 17/7001* (2013.01); *A61B 17/866* (2013.01); *F04C 2270/0421* (2013.01)

(58) Field of Classification Search
CPC .................................................... A61B 17/844
See application file for complete search history.

(56) References Cited

U.S. PATENT DOCUMENTS

| | | | |
|---|---|---|---|
| 4,610,587 | A | 9/1986 | Lvollar et al. |
| 4,711,232 | A | 12/1987 | Fischer et al. |
| 4,716,893 | A | 1/1988 | Fischer et al. |
| 5,019,079 | A | 5/1991 | Ross |
| 5,868,749 | A | 2/1999 | Reed |
| 6,048,343 | A | 4/2000 | Mathis et al. |
| 6,290,700 | B1 | 9/2001 | Schmotzer et al. |
| 6,325,805 | B1 | 12/2001 | Ogilvie et al. |
| 6,733,506 | B1 | 5/2004 | McDevitt et al. |

(Continued)

FOREIGN PATENT DOCUMENTS

| | | |
|---|---|---|
| CN | 87206406 U | 3/1988 |
| CN | 1863489 A | 11/2006 |

(Continued)

OTHER PUBLICATIONS

Chinese Search Report for Application No. CN2013800246325 dated Mar. 23, 2016.

(Continued)

*Primary Examiner* — Andrew Yang
(74) *Attorney, Agent, or Firm* — Howard & Howard Attorneys PLLC

(57) ABSTRACT

The present invention relates to a bone-fixation anchor comprising a rigid expandable part and a soft part. The rigid expandable part secures the anchor with respect to the bone and the soft part enables the anchor to fit any bone screw on the market.

19 Claims, 10 Drawing Sheets

(56) References Cited

U.S. PATENT DOCUMENTS

| | | |
|---|---|---|
| 6,939,135 B2 | 9/2005 | Sapian |
| 7,875,059 B2 | 1/2011 | Patterson et al. |
| 8,221,479 B2 | 7/2012 | Glazer et al. |
| 8,388,660 B1 * | 3/2013 | Abdou ............... A61B 17/8685 606/267 |
| 8,911,484 B2 | 12/2014 | Lei et al. |
| 2002/0019636 A1 | 2/2002 | Ogilvie et al. |
| 2002/0035366 A1 | 3/2002 | Walder et al. |
| 2003/0153919 A1 | 8/2003 | Harris |
| 2004/0116932 A1 | 6/2004 | Mazda et al. |
| 2004/0176767 A1 | 9/2004 | Bickley |
| 2005/0055096 A1 | 3/2005 | Serhan et al. |
| 2005/0240188 A1 | 10/2005 | Chow et al. |
| 2005/0277940 A1 | 12/2005 | Neff |
| 2006/0009768 A1 | 1/2006 | Ritland |
| 2006/0167459 A1 | 7/2006 | Groiso |
| 2006/0235410 A1 | 10/2006 | Ralph et al. |
| 2006/0241593 A1 | 10/2006 | Sherman et al. |
| 2006/0276788 A1 | 12/2006 | Berry et al. |
| 2007/0016193 A1 | 1/2007 | Ritland |
| 2007/0118131 A1 | 5/2007 | Gooch |
| 2008/0039846 A1 | 2/2008 | Lee et al. |
| 2008/0140122 A1 | 6/2008 | Bethell |
| 2008/0154308 A1 | 6/2008 | Sherman et al. |
| 2009/0005821 A1 | 1/2009 | Chirico et al. |
| 2009/0062868 A1 | 3/2009 | Casutt |
| 2009/0177229 A1 | 7/2009 | Gulotta et al. |
| 2010/0204734 A1 | 8/2010 | Renaud |
| 2011/0144766 A1 | 6/2011 | Kale et al. |

FOREIGN PATENT DOCUMENTS

| | | |
|---|---|---|
| CN | 102119007 A | 7/2011 |
| EP | 1206924 A1 | 5/2002 |
| EP | 1743587 A1 | 1/2007 |
| JP | 2002282258 A | 10/2002 |
| JP | 2002541970 A | 12/2002 |
| JP | 2004528945 A | 9/2004 |
| WO | 9837825 A1 | 9/1998 |
| WO | 02102259 A2 | 12/2002 |
| WO | 2005041795 A1 | 5/2005 |
| WO | 2009155577 A2 | 12/2009 |

OTHER PUBLICATIONS

International Search Report for Application No. PCT/EP2013/055015 dated Jul. 1, 2013.

PCT International Search Report dated Jul. 1, 2013, Application No. PCT/EP2013/055015, 5 pages.

PCT International Search Report dated Nov. 27, 2008 for Application No. PCT/FR2008/500700.

* cited by examiner

UNIVERSAL ANCHOR FOR BONE FIXATION

This application is a continuation of U.S. patent application Ser. No. 14/385,125, filed Sep. 12, 2014, which in turn is a 35 U.S.C. § 371 national stage entry of PCT/EP2013/055015, which has an International filing date of Mar. 12, 2013 and which claims priority to U.S. Provisional Patent Application No. 61/609,728, filed Mar. 12, 2012. The disclosures of each of the above applications are incorporated herein by reference in their entireties.

FIELD OF INVENTION

The present disclosure relates generally to the field of bone fixation. More particularly, the disclosure relates to bone anchors for use with bone-fixation screws, such as particular screws, for any application, including, for example, osteosynthesis. Some embodiments of the present disclosure are particularly useful in osteoporotic bones.

BACKGROUND OF INVENTION

Skeletal structures are formed of bones and adjoining structures. These skeletal structures may require artificial support or stabilization. For example, the human spine is composed of a column of thirty-three vertebrae and their adjoining structures. Most of the vertebrae are capable of individual movement and ensure the general movement of the spine: flexion, extension, axial rotation and lateral flexion. An intervertebral disc is positioned between opposing faces of adjacent vertebrae. Each of these vertebrae includes a vertebral body, and a vertebral arch that encloses an opening, called the vertebral foramen, through which the spinal cord and spinal nerves pass. The body of the spinal vertebra is connected to the arch by the pedicles—one on either side of the arch—, which form two short thick processes. Unfortunately, there are numerous diseases that deteriorate one or more portion of the vertebra. For example, osteoporosis, scoliosis, kyphosis, spondylolisthesis, tumors, as well as fractures or extreme shocks may leads to the deterioration of vertebrae. As a result vertebrae may collapse, nerves may be pinched causing enormous pain, or regular movement of the column may be limited. In these and other situations, surgical installation of various devices is designed to allow the person to resume a normal life.

One well-known device for spine stabilization procedures is the pedicle screw, which is threaded for engagement with bone. A pedicle screw is surgically installed posteriorly into and through a pedicle. Bone screws, like pedicle screws, are commonly used to fix adjacent bones or bone fragments with respect to each other. For example, bone screws are commonly used to help repair fractures in bone, to attach bone plates to bone, to fix adjacent vertebral bodies, or for stabilizing the spine. When the bone is diseased, for example due to osteoporosis, deteriorated, for example due to prior surgical procedure, or degenerated, securing the bone screw may be problematic. For instance, when a pedicle screw is used on osteoporotic patients, the lack of bone density makes it difficult to properly engage the bone screw threads within the pedicle resulting in a fragile connection between the pedicle screw and bone.

Technical Issues

If the threaded portion of the screws does not properly secure to the bone, the bone screw will loosen and pull out or break. This loosening can occur over time. Therefore one of the issues intended to be solved by this invention is to provide an anchor system with improved fixation to bone. The anchor of the present invention is first inserted into the bone and ensures fixation with respect to the bone. The bone screw is then inserted into the anchor and the anchor ensures fixation with respect to the bone screw. Therefore the bone screw is better secured when inserted in the anchor, and the anchor ensures an efficient fixation between the bone and the bone screw.

Most of the orthopedic device manufacturers are currently selling bone screws with various shapes, sizes or diameters. Therefore another issue to be solved by this invention is to provide a universal anchor compatible with most of the bone screws on the market.

As bone screws present threads, they can be removed by unscrewing once the bone has been stabilized. The removal of the bone screw is necessary to avoid leaving unnecessarily foreign body inside the human body. However anchors, and especially expandable anchors, present hollows and asperities, into which bone may grow, preventing the ability to remove the anchors. As bone screws may be removed, it is another issue of the present invention to achieve removable anchors.

SUMMARY

In one embodiment, a bone-fixation anchor (1) comprises a first part of soft material; and a second part which is deformed when the screw (2) is inserted into the anchor.

In one embodiment, said second part is made of a material more rigid than the first part.

In one embodiment, the anchor (1) further comprises a third part comprising blocking means for preventing rotational or translational movement of the anchor (1) when inserted into a bone.

In one embodiment, said second part comprises anchor blades (3).

In one embodiment, said anchor blades (3) may expand and secure the anchor with respect to the bone.

In one embodiment, the anchor (1) further comprises a means for preventing bone growth inside the anchor.

In one embodiment, the anchor (1) further comprises at least one sliding part (5) in the thickness of the anchor blades and between the anchor blades (3), preventing bone from filling the free space inside the anchor.

In one embodiment, said anchor blades (3) comprise means for cutting newly formed bone.

In one embodiment, the anchor (1) further comprises means for closing the anchor blades.

In one embodiment, the anchor (1) further comprises an external thread for screwing and unscrewing the anchor.

In one embodiment, the anchor (1) comprises a helical opening adjusted with respect to the bone screw thread and providing an anchorage when said thread stands out of the anchor.

In one embodiment, the anchor (1) further comprises an interior made of a soft material.

In one embodiment, the anchor (1) further comprises an exterior made of a rigid material.

In one embodiment, the anchor further comprises a tapering distal end.

In one embodiment, the anchor further comprises a non-uniform cross-section.

In one embodiment, the anchor (1) is used with a bone screw (2).

In an embodiment, the anchor (1) is inserted inside a bone, such as for instance inside a vertebra through a pedicle.

DEFINITIONS

In the present invention, the following terms have the following meanings:

"Compatible" refers in the present invention to the ability for any bone screw on the market to be used, in operational conditions, with the anchor of the present invention.

"Expanded" or deformed refers in the present invention to an increase, in at least one dimension, of the size of the anchor with respect to the initial condition; in order to secure the anchor with respect to the bone.

"Secure" refers in the present invention to the ability, in use, to maintain the different parts of the present invention in the desired position.

"Soft" or deformable refers in the present invention to the adaptability to the surrounding elements by deformation. For the purpose of this invention, materials may be considered soft when their young's modulus is inferior to 10 GPa.

"Rigid" or hard refers in the present invention to the ability to resist deformation. For the purpose of this invention, materials may be considered rigid when their young's modulus exceeds 10 GPa. The young's modulus is measured from conventional means known by any person skilled in the art.

DETAILED DESCRIPTION

This invention relates to a universal anchor for bone fixation. Embodiments of the present disclosure provide a universal anchor, which may be used with any bone fixation screw, such as a pedicular screw, in a bone (e.g. an osteoporotic bone). The anchor may be, for example, inserted inside a pedicle, and may be configured to be compatible with various screws on the market (e.g. pedicle screws having various profiles and/or pitches). In the embodiment of FIG. 1, the anchor 1 has been inserted into a bone, and a bone screw 2 has been partially screwed into the anchor. According to some embodiments, the anchor 1 may be used during a reoperation (e.g. when there is a bone defect which prevents the anchoring).

According to a first embodiment of the present disclosure, the anchor 1 includes various parts, which may be made of different materials. For example, as shown in FIG. 2, the anchor 1 may include:

A first part B having a smaller diameter than the screw 2 or the rest of the anchor 1 such that the screw thread engages in the inner diameter of said first part. The first part B allows a fixation between the anchor 1 and the screw 2, and may be made of a soft material. This intermediate part B is specifically designed in order to fit any bone screw 2 on the market. The diameter of the intermediate part B is about the diameter of the core of the bone screw 2.

A second part C which is deformed upon insertion of the screw 2 and when the screw 2 is inserted to allow the anchoring of the anchor 1 in the bone (e.g. in the vertebral body). The second part C may be made of a much more rigid material (e.g. compared to the first part). In one embodiment the ratio of the young's modulus of the rigid part on the young's modulus of the soft part is at least 2. This distal part C is designed, in use, to expand and secure the anchor with respect to the bone.

A third part A, including means for preventing a rotational movement of the anchor 1 when the anchor is inserted in the bone. The proximal part A may be provided at or near a posterior end of the anchor 1 to block the anchor from a translational movement. The third part A may also be configured to enable the anchor 1 to be removed later, when necessary.

These three parts of the anchor and their technical implementations provide various innovative features described hereafter.

Internal Anchorage

In one embodiment, the distal part C of the anchor 1 comprises means for securing the anchor 1 inside the bone. In another embodiment, the distal part C of the anchor 1 comprises at least one expandable part ensuring the anchorage of the anchor 1 with respect to the bone. In one embodiment, the means situated in distal part C of the anchor 1 are designed to expand, behind the pedicle, inside the vertebral body. In an embodiment, the means for securing the anchor 1 inside the bone are at least one blade 3, preferably at least two blades 3.

In the embodiment of FIG. 2, the anchor 1, before use, ready for insertion, is in closed position. In the embodiment of FIG. 3, the anchor 1, in use, is in opened position (the bone screw is not represented). The blades 3 (i.e. the means for securing the anchor 1), located at the distal part C of the anchor 1, present specific shapes allowing the expansion of the blades 3 upon insertion of the screw 2. In one embodiment, said specific shapes comprise for instance a beveled face, a tapering end or any other means that a person skilled in the art would find suitable. In one embodiment, all blades 3 have the same specific shape.

In one embodiment, the means located at the distal part C of the anchor 1 are designed to expand in at least one direction. In one embodiment, the means located at the distal part C of the anchor 1 are designed to expand in at least two directions. In one embodiment, the means located at the distal part C of the anchor 1 are designed to expand in at least four directions. The anchor 1 expands in various directions according to the number of anchor blades 3 and to the shape of the distal part C. In one embodiment, the expanding of the anchor blades 3 may be symmetrical or not.

In an embodiment, the means for securing the anchor is molded and/or extruded as a single piece of work with respect to the anchor 1.

In one embodiment, the distal part C of the anchor 1 comprises at least one expandable part preventing removal of the anchor 1 out of the bone. In another embodiment, means ensuring the removal of the anchor 1 after use are also implemented. These means are fully described hereafter.

Bone Growth Prevention

In one embodiment, the anchor 1 provides means or device to maintain the anchor 1 in a closed position in order to prevent the bone from growing and to help the removal of the anchor 1. In another embodiment, the anchor 1 comprises means for preventing the bone growth. In one embodiment, the anchor 1 comprises means for helping the removal of the anchor 1 after use.

In some embodiments of the present disclosure, the anchor 1 may be configured to prevent bone growth in the area near the anchor 1 after placement. In one embodiment, the anchor 1 and/or the screw 2 may be intended to be removed from the human body. Particularly, concerning the removable part of the anchor 1, it should be kept in mind that once inserted in the bone (e.g. the vertebral body), bone growth may occur in any gap around the anchor 1, which may prevent the closing and removal from the anchor 1. When the anchor 1 expands, it is also important to avoid that the bone grows in the free-space. To address this, the present disclosure provides several features to help the removal:

1—A flexible covering around the anchor 1 preventing the bone from filling the gaps. In the embodiment of FIG. 4, the anchor 1 comprises a cover 4 around the anchor 1 preventing the bone from filling the gaps. In one embodiment, the anchor 1 comprises a flexible cover. In one embodiment, the anchor 1 comprises a cover 4 only on the distal part C.

2—Configuring the anchor blades 3 to reduce any gap between the anchor 1 and the bone (e.g. as much as possible, or even to eliminate the gap). In one embodiment shown in FIG. 5, the anchor blades 3 comprise at least one sliding part 5. In one embodiment, the anchor 1 comprises, in the thickness of the anchor blades 3 and between the anchor blades 3, sliding parts 5 allowing the expanding of the anchor blades 3 while preventing the bone from filling the free-space.

3—Configuring the anchor blades 3 to cut any newly formed bone. In one embodiment, the anchor blades 3 comprise means for cutting newly formed bone. In the embodiment of FIG. 6, the anchor blades 3 comprise at least one cutting edge 6. In one embodiment, the anchor blades 3 comprise at least one beveled cutting edge.

4—Providing a mechanism to push the blades 3 and have a stronger force to close them. In one embodiment, the anchor 1 comprises means for closing the anchor blades 3 in order to remove the anchor 1. In the embodiment of FIG. 7, proximal and intermediate parts A and B are divided into an outer portion 7 and an inner portion 8. In one embodiment, said inner and outer portions can move with respect to each other. In one embodiment, said outer portion 7 may be screwed on said inner portion 8. In one embodiment, the anchor blades 3 are linked to said inner portion 8 and said outer portion 7 can push the anchor blades 3 and close them. In this embodiment, the outer portion 7 pushes over the anchor blades 3 during screwing on the inner portion 8, and closes the anchor blades 3.

5—Providing means (such as for example a system with elastic ring(s) 9 to close the anchor 1 when the screw is removed. In an embodiment, devices are implemented in order to close the anchor 1 once the bone screw 2 is removed. In the embodiment of FIG. 8, at least one elastic ring 9 linking the anchor blades closes them once screw 2 is unscrewed.

External Holding

In one embodiment, the proximal part A of the anchor 1 includes means for preventing the movement of the anchor 1 once the anchor 1 is inserted. In one embodiment, the means for preventing the movement of the anchor 1 are provided at the posterior end of the anchor 1. In one embodiment, the means for preventing the movement of the anchor 1 are provided near the posterior or rear end of the anchor 1.

In an embodiment, the proximal part A of the anchor 1 comprises means preventing the rotational and/or translational movement of the anchor 1 during use. These means would be those that a person skilled in the art would find suitable. According to some embodiments of the present disclosure, for example, as shown in FIG. 9, means for preventing a rotational movement of the anchor 1 in the bone may be provided. As shown, fins 10 are provided to block any rotation in the bone. In an embodiment, means such as fins or notches 10 are provided for preventing a rotational movement of the anchor 1 in the bone. These fins or notches 10 hook on the bone and prevent rotation. In another embodiment, the proximal part A comprises a larger diameter at the posterior end, preventing the full insertion of the anchor 1 inside the bone and preventing the translational movement.

In an embodiment, the means preventing the rotational and/or translational movement of the anchor 1 is molded and/or extruded as a single piece of work with respect to the anchor 1. In another embodiment, the means preventing the rotational and/or translational movement of the anchor 1 is molded or injection molded separately and then connected to the anchor 1 by any suitable means.

In one embodiment, the proximal part A is configured to enable the anchor 1 to be removed, even many years after insertion. In one embodiment, the anchor 1 comprises a flange enabling easy removal of the anchor. In another embodiment, the proximal part A of the anchor 1 comprises at least one notch allowing the screwing and unscrewing of the anchor.

As shown in FIG. 10-13, according to some embodiments of the present disclosure, the anchor 1 is suitable for placement in the vertebra for fixation with a screw 2.

Pedicle Burst Prevention

In one embodiment, the anchor 1 prevents the pedicle from inflating and/or bursting.

According to some embodiments of the present disclosure, for example, as shown in FIG. 14, the interior of the anchor 1 may be provided with or made of a soft material for screw fixation, while the exterior of the anchor 1 may be made of a hard material to prevent inflation. The distal part C of the anchor 1 of the present invention may expand but the intermediate part B and the proximal part A do not expand, preventing excessive deformation of the intermediate and proximal parts.

In an embodiment, the proximal part A and/or the intermediate part B comprises on their inner surface 11 a soft material adapted to receive most of the pedicle screws on the market. The soft material is thick enough to ensure contact with thin screws and comprise a soft material that may be deformed to allow the insertion of large screw. During insertion, the thread of the screw and/or the body of the screw deformed the soft material and ensure good fixation for every bone screw 2. In one embodiment, the bone screw 2 is screwed to the anchor 1 on the proximal and/or intermediate parts thanks to said inner soft surface 11. In one embodiment, the outer surface 12 of the proximal part A and/or intermediate part B comprises a rigid material. The rigid material prevents an excessive deformation of the intermediate and proximal parts of the anchor, which could leads to the burst of the bone, such as the pedicle. In one embodiment, a pipe of soft material forming the inner surface 11 is rigidly connected to the outer surface 12. In the present invention soft has the same meaning as smooth.

In one embodiment, the anchor 1 is made or coated from polymers like polyethylene, polypropylene, polycarbonate, polyurethane or other materials of equivalent characteristics.

In one embodiment, the anchor 1 is made or coated from elastomers In one embodiment, the rigid part 12 is made or coated from polymers like PEEK, polycarbonate, polyurethane, or composite materials or other materials with equivalent characteristics.

In one embodiment the soft part 11 is made or coated from silicon or polyethylene or other materials with equivalent characteristics of elasticity or deformability.

In one embodiment, the anchor may be partially or totally coated with a material, which differs or not from the material it covers.

Adaptation to Screw Design

In one embodiment, the inner distal part of the anchor 1 is adapted to the screw in order to leave less space possible for bone growth. In one embodiment, the outer distal part of the anchor 1 is adapted to the screw 2 in order to leave less space possible for bone growth.

According to some embodiments of the present disclosure, for example, as shown in FIGS. 15 and 16, the anchor 1 may have a "closed" configuration, having a tapering distal portion. In the embodiment of FIGS. 15 and 16, the anchor 1, in initial closed position, comprises a tapering distal portion. When the bone screw 2 is inserted inside the anchor 1, the tapering distal portion expands. The tapering distal portion ensures to leave less space possible for bone when inserting as well as in use. This tapering distal portion facilitates the insertion, minimizes the free space for bone and ensures efficient fixation when expanded.

According to some embodiments of the present disclosure, for example, as shown in FIG. 17, the anchor 1 may be configured to reduce any gap to prevent bone growth in the gap region. In this embodiment, the thread of the bone screw is anchored inside the soft material of the intermediate part B. In one embodiment, the inner intermediate part comprises a thread designed to fit the thread of the bone screw 2. In one embodiment, the inner intermediate part comprises a soft material filling most of the intermediate part B in order to let the screw make its way through the soft material.

In one embodiment, the inner distal part C comprises a thread designed to fit the thread of the bone screw 2. In one embodiment, the inner distal part comprises a soft material filling most of the distal part C, preventing the bone growth while still allowing the insertion of the bone screw 2.

Threaded Part

In one embodiment, the anchor 1 provides a threaded part in the pedicle area (e.g. to ease the insertion and/or possible removal of the anchor).

According to some embodiments of the present disclosure, for example, as shown in FIG. 18, the anchor 1 may have an external threaded part to ease the insertion and/or possible removal of the anchor 1. In an embodiment, the anchor 1 comprises on the intermediate part B and/or on the proximal part A an external thread that enables the insertion of the anchor 1. In another embodiment, the anchor 1 may be inserted by impaction. In an embodiment, the anchor 1 comprises on the intermediate part B and/or on the proximal part A an external thread that enables the removal of the anchor 1, which closes the expanded distal part C.

Different Designs

In one embodiment, a design specifically adapted to pedicle morphology is implemented. Its vertical insertion allows a good fit in the pedicle. It also provides a different way to interfere with the pedicle screw (kind of thread).

In some embodiments of the present disclosure, for example, as shown in FIGS. 19-21, the anchor 1 may have a non-uniform cross-section from the proximal end to the distal end. For example, as shown in FIG. 20, the anchor 1 has substantially cylindrical proximal A and intermediate B portions, and a non-cylindrical distal portion C (e.g. having a substantially elliptical, oval, egg, or rectangular cross-section). The shape of the distal portion C may be adapted to suit the bone into which the anchor 1 is inserted. For example, as shown in FIG. 21, the anchor 1 for insertion into the pedicle is configured to have an almost elliptical or oval cross-section at the distal end C.

In one embodiment, the intermediate portion B comprises at least one reinforcement piece 13. In a preferred embodiment, the intermediate portion B comprises two reinforcement pieces 13 on the superior and inferior aspect of portion B. In the embodiment of FIG. 19, the intermediate portion B features 2 longitudinal webs 13 extending on the superior and inferior aspect of portion B.

Also as shown, for example, in FIGS. 19-21, in some embodiments of the present disclosure, the anchor 1 may be designed to adjust to the thread of the pedicle screw. In one embodiment, the intermediate part B of the anchor 1 comprises a helical opening representing an opened thread. In the embodiment of FIG. 22, the anchor 1 comprises a helical opening adjusted to fit the thread of the bone screw 2. In the embodiment of FIG. 23, the thread of the screw 2 stands out of the helical opening of the anchor 1 and ensures an additional anchorage.

Although anchor 1 for use with pedicular screws 2 are discussed above and shown herewith, it would be clear to one skilled in the art that the anchors 1 may also be with other types of screws and/or for other types of bone fixation.

In an embodiment, the anchor 1 is suitable for insertion into any bone and for use with any bone screw 2. In an embodiment, the anchor 1 is suitable for insertion into a vertebra and for use with a bone screw 2. In another embodiment, the anchor 1 is suitable for insertion into a vertebra and for use with a pedicle screw 2.

BRIEF DESCRIPTION OF THE DRAWINGS

The present invention is further illustrated by the following drawings. It should be understood that the instant application is not limited to the precise arrangement illustrated in the drawings, in which.

LIST OF REFERENCES

Figure 1:
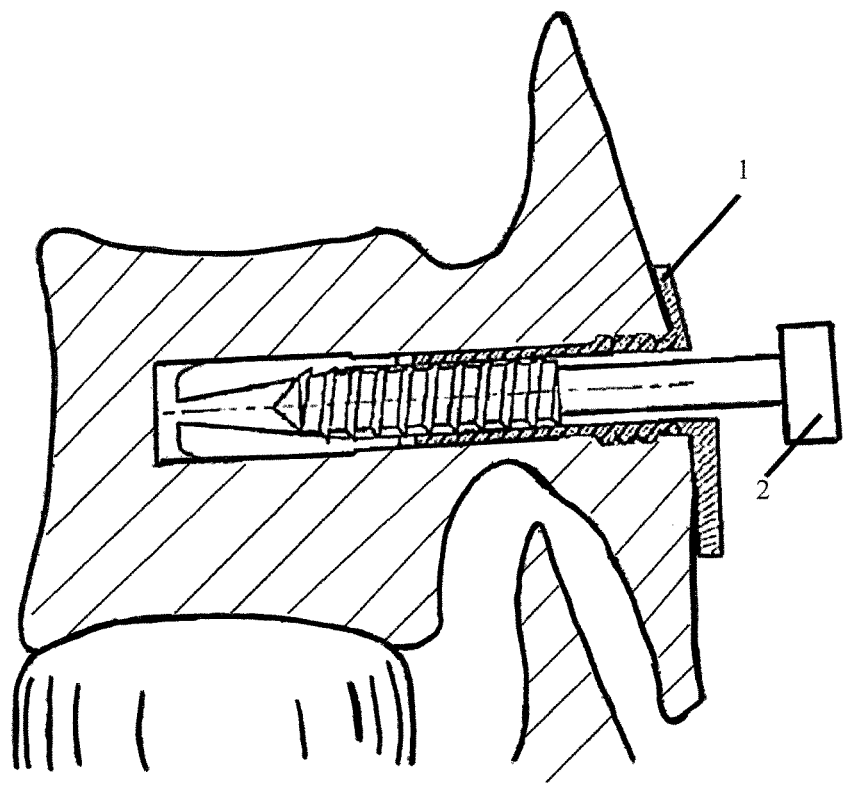
FIG. 1 shows a sectional-view of an anchor 1 inserted into a vertebra during use with a pedicle screw 2.
Figure 2:
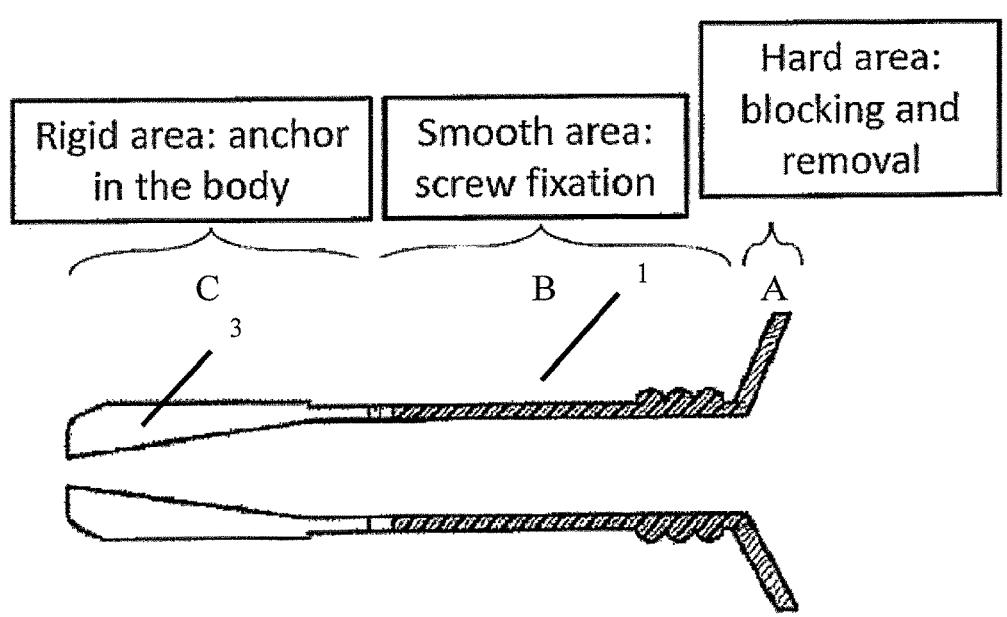
FIG. 2 shows an anchor 1 including three portions: a rigid distal portion C to be anchored in the bone, a soft intermediate area B for screw fixation, and a hard proximal area A for blocking (e.g. preventing a rotational movement of the anchor in the bone) and possible removal of the anchor later, if desired. As shown, the anchor 1 is in an initial closed position, ready for insertion.
Figure 3:
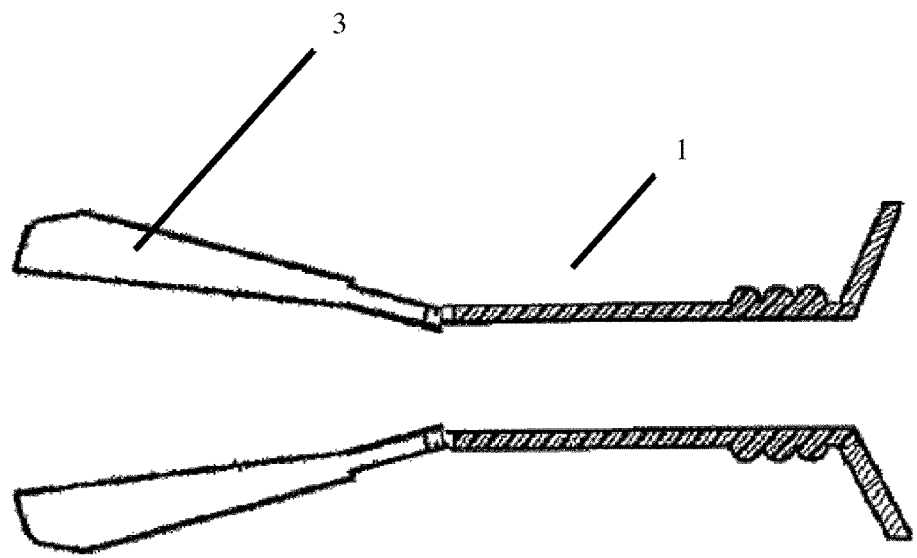
FIG. 3 shows an anchor 1 with the anchor blades 3, in use (i.e. with the distal portion in an opened position).
Figure 4:
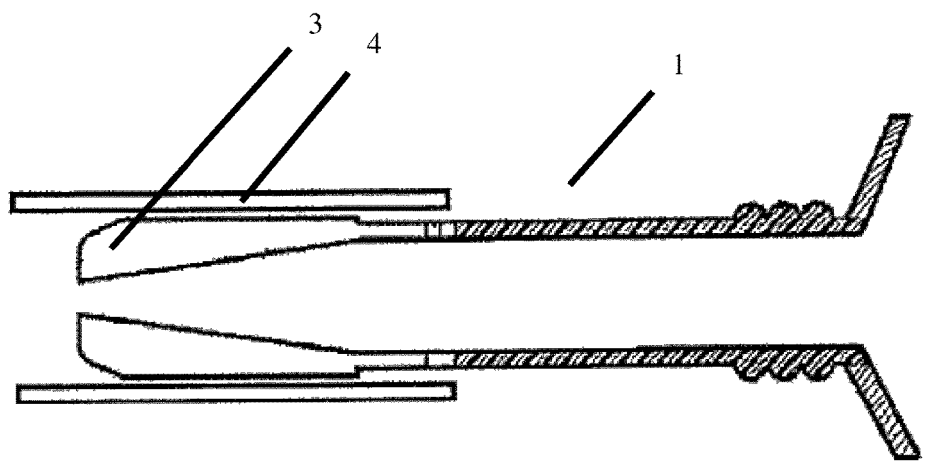
FIG. 4 shows an anchor 1 and the anchor blades 3 with a covering 4 preventing the bone from filling the gap (a flexible cover around the expanding area prevents bone insertion).
Figure 5:
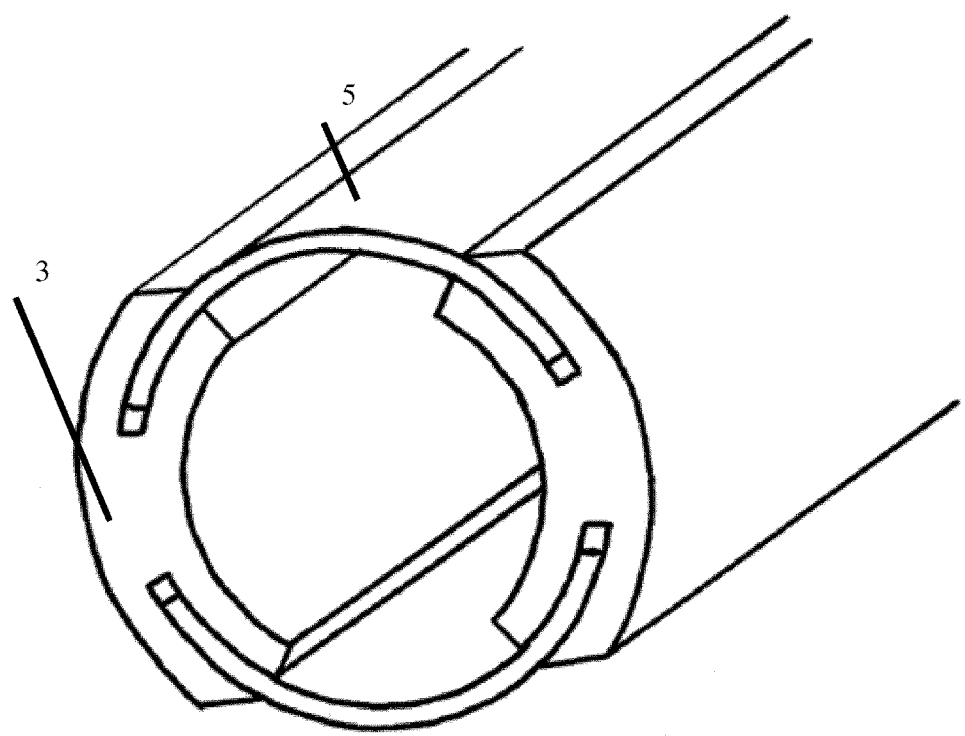
FIG. 5 shows an anchor 1 configured such as the anchor blades 3 reduce the gap between the anchor and the bone thanks to a sliding part 5 (designed with smallest gap possible).
Figure 6:
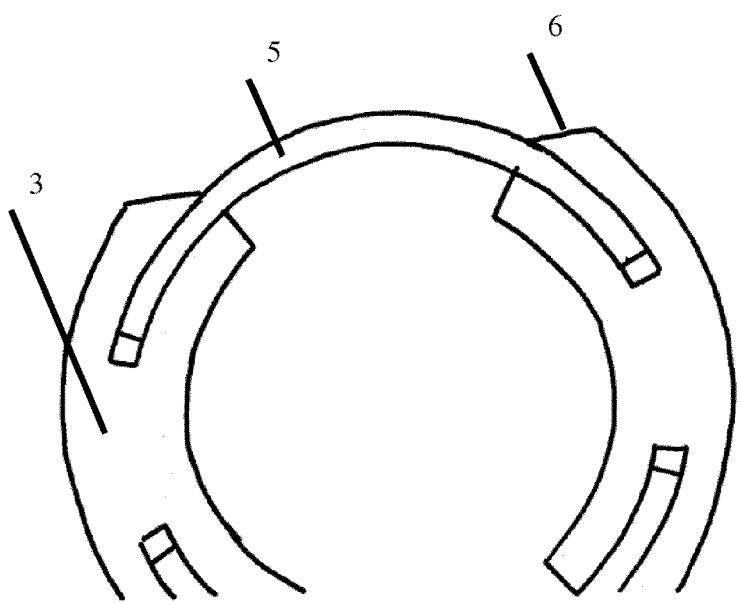
FIG. 6 shows an anchor 1 configured such as the anchor blades 3 may cut any neo-formed bone thanks to a cutting edge 6 (design of the blades to cut any neo-formed bone).
Figure 7:
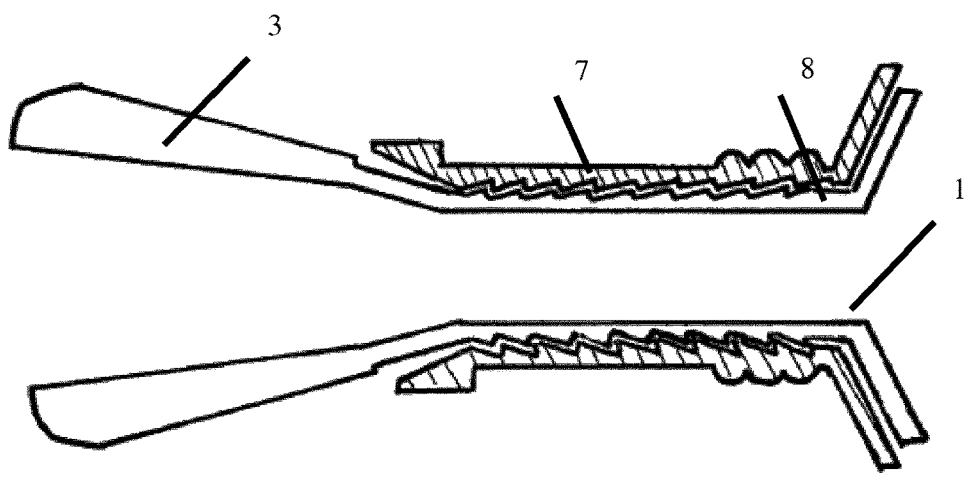
FIG. 7 shows an anchor 1 with an outer shell 7 allowing to push the anchor blades 3 and to close them (mechanism to push the blades and close it with higher force: internal part 8 is maintained blocked, external part 7 is screwed on the red part and pushes the blades).
Figure 8:
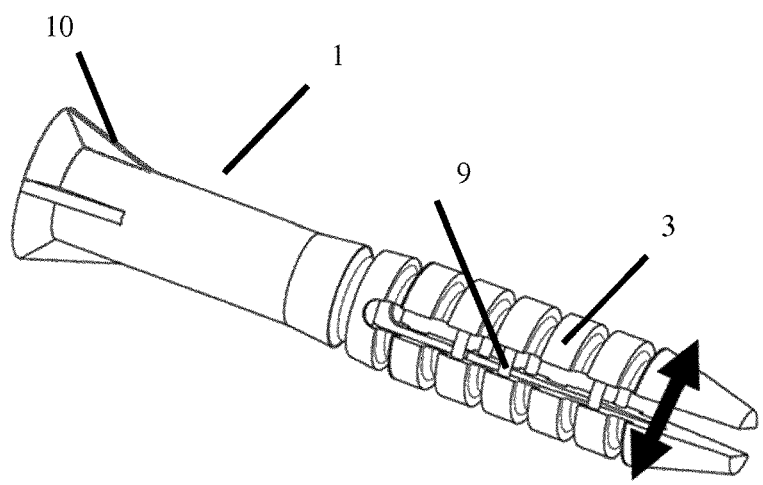
FIG. 8 shows an anchor 1 with elastic rings 9 between the anchors blades 3 that close the anchor when the screw 2 is removed (elastic ring keeps the blades close once screw is unscrewed).
Figure 9:
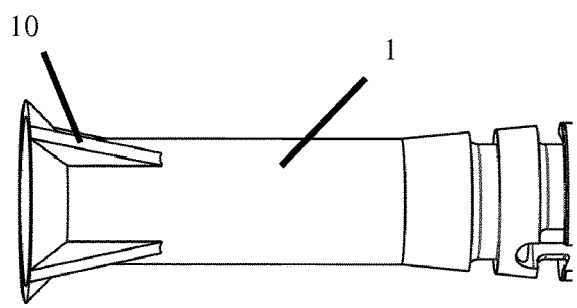
FIG. 9 shows an anchor 1 configured such as to prevent rotational movement of the anchor in the bone (4 shapes 10 blocks the rotation in the bone).
Figure 10:
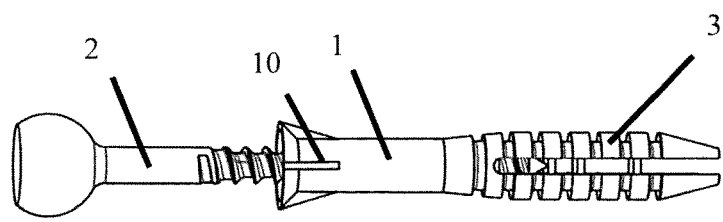
FIG. 10 shows the assembly of an anchor 1 and a pedicle screw 2 during insertion.
Figure 11:
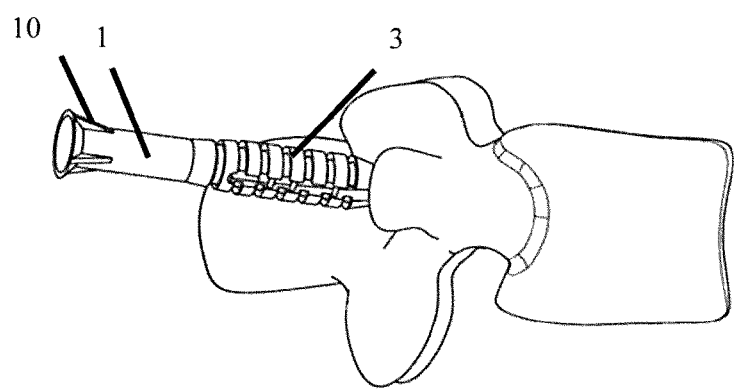
FIG. 11 shows an anchor 1 before insertion in a vertebra (it illustrates the placement of the anchor in the vertebra).
Figure 12:
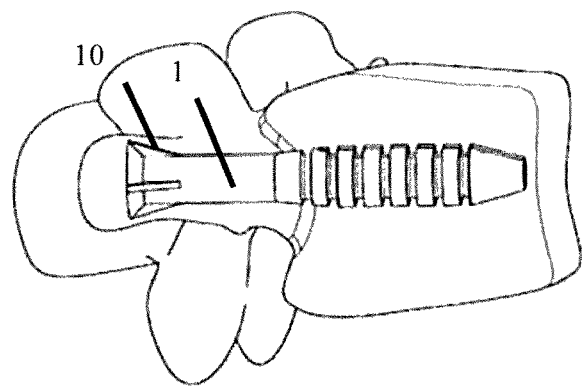
FIG. 12 shows, by transparency, an anchor 1 after insertion in a vertebra.
Figure 13:
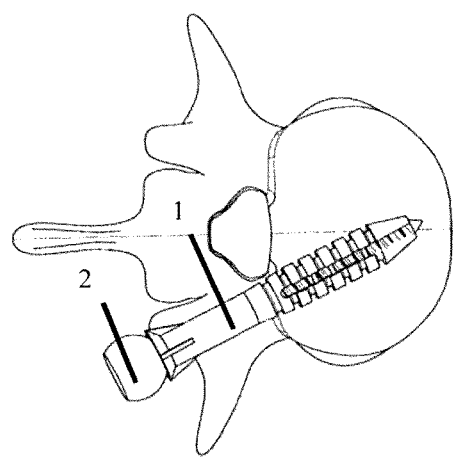
FIG. 13 shows, by transparency, an anchor 1 in use with a pedicle screw 2 after insertion in a vertebra (fixation of the screw in the anchor)
Figure 14:
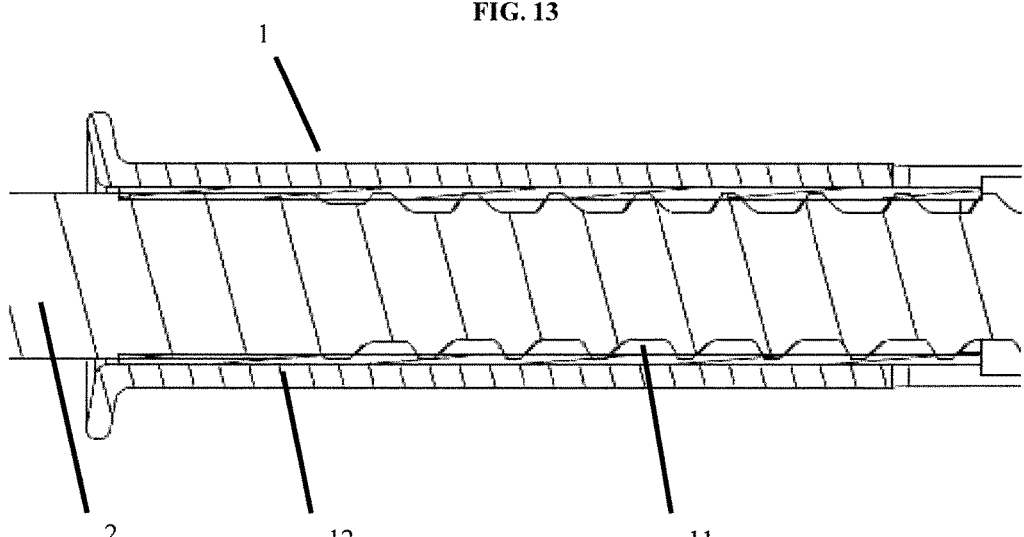
FIG. 14 shows a composite anchor 1 with an inner soft material 11 for screw fixation and an outer hard material 12 to prevent inflation. The bone screw thread deforms the inner soft material 11; this leads to the anchorage of the bone screw 2 with respect to the anchor 1.
Figure 15:
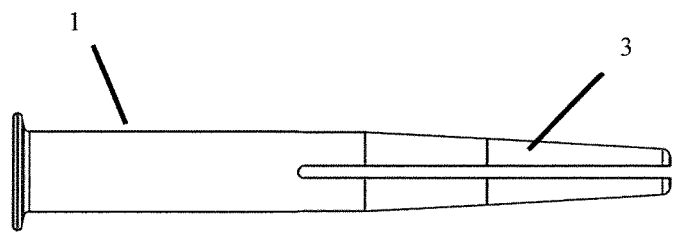
FIG. 15 shows a side view of an anchor 1 with anchor blades 3; having a tapering distal portion.
Figure 16:
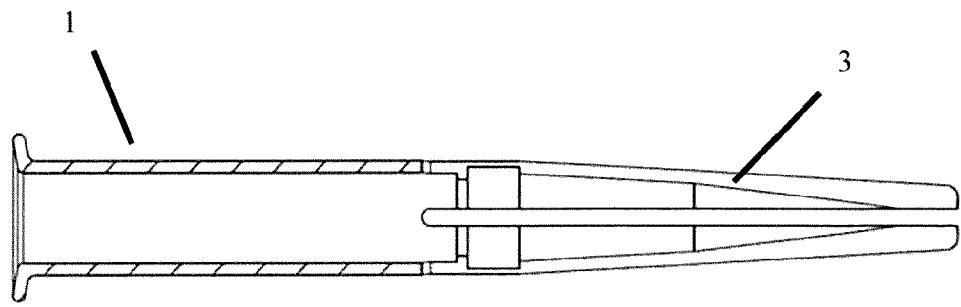
FIG. 16 shows a sectional view of an anchor 1, with anchor blades 3, in initial closed position having a tapering distal portion
Figure 17:
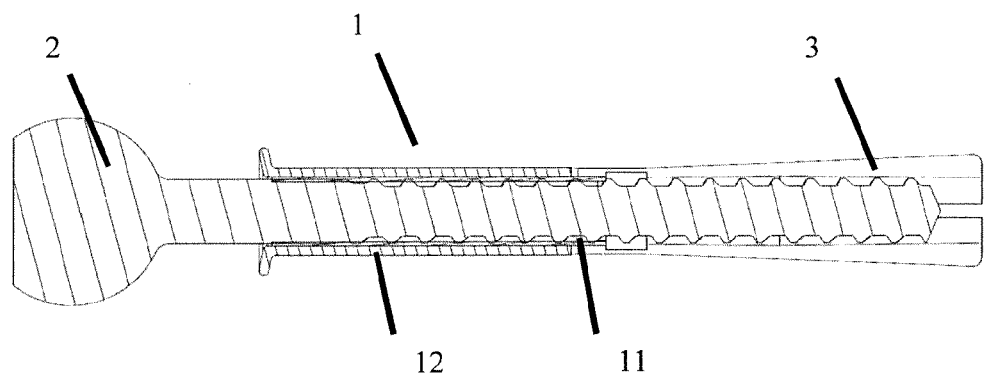
FIG. 17 shows a sectional view of a composite anchor 1 having the smallest gap possible to prevent bone growth. The insertion of the bone screw 2, inside the soft part of the anchor 1 is represented.
Figure 18:
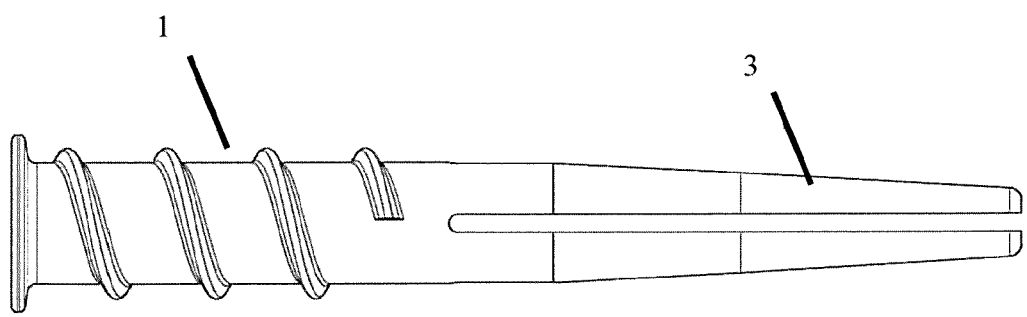
FIG. 18 shows an anchor 1 with an external threaded part.
Figure 19:
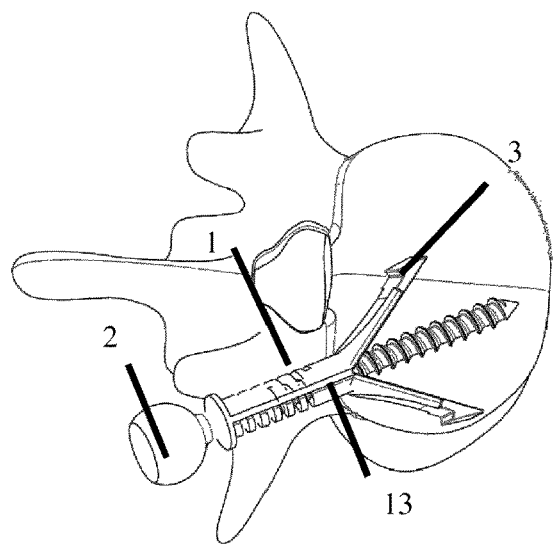
FIG. 19 shows, by transparency, an anchor 1 after insertion in a vertebra, in opened position, with a non-uniform cross-section and a screw 2. It also discloses a reinforcement piece 13.
Figure 20:
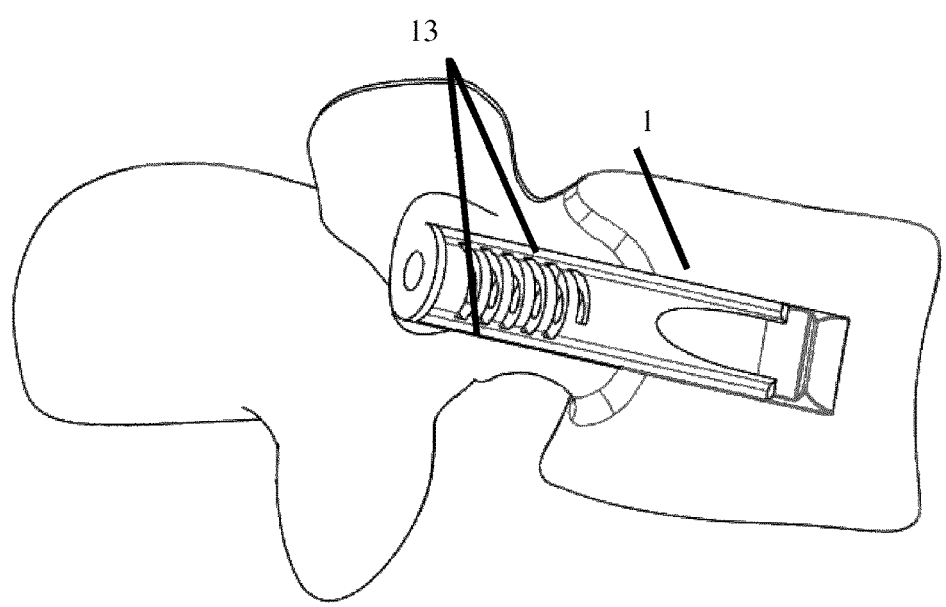
FIG. 20 shows a side-view, by transparency, of an anchor 1 after insertion in a vertebra, in initial closed position with a non-uniform cross-section: a substantially cylindrical proximal A and intermediate B portions and a non-cylindrical distal portion C. It also discloses the reinforcement pieces 13.
Figure 21:
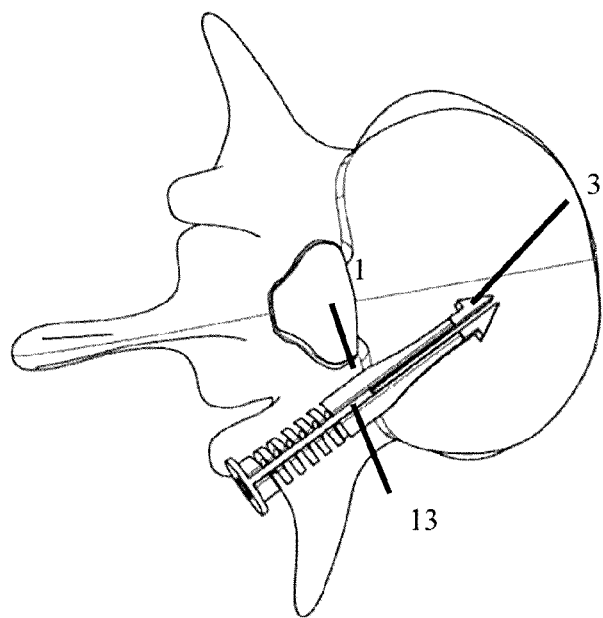
FIG. 21 shows a top view, by transparency, of an anchor 1 after insertion in a vertebra, in initial closed position with a non-uniform cross-section: a substantially cylindrical proximal A and intermediate B portions and an almost elliptical or oval distal portion C. It also discloses a reinforcement piece 13.
Figure 22:
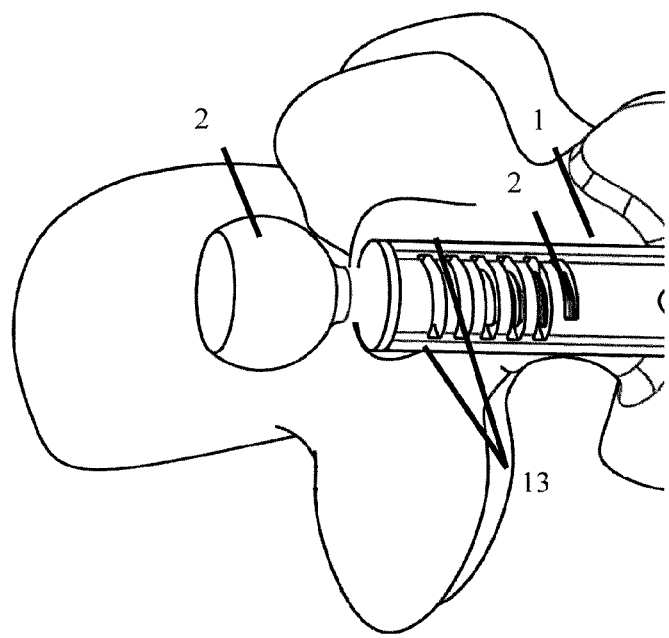
FIG. 22 shows, by transparency, an anchor 1 after insertion in a vertebra, having a helical opening on the intermediate portion B for adjusting the pedicle screw thread. It also discloses a reinforcement piece 13. In the shown embodiment, the thread of the bone screw 2 does not stand out of the anchor 1.
Figure 23:
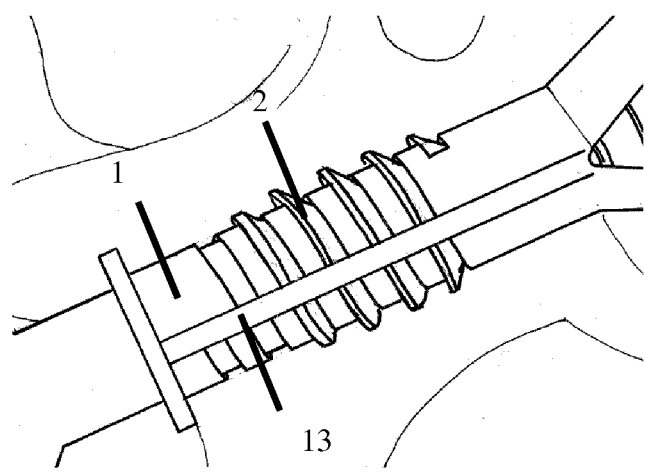
FIG. 23 shows, by transparency, an anchor 1 after insertion in a vertebra, having a helical opening on the intermediate portion B; and a screw 2. The thread of the screw 2 is configured to fit the opened thread of the anchor 1 and ensure an additional anchorage when the thread of the bone screw 2 stands out of the anchor 1. It also discloses a reinforcement piece 13.

A Proximal part
B Intermediate part
C Distal part
1 Anchor
2 Bone screw
3 Anchor blade
4 Covering
5 Sliding part
6 Cutting edge
7 Outer portion
8 Inner portion
9 Elastic ring
10 Fins
11 Inner surface with soft material for screw fixation
12 Outer surface with hard material to prevent inflation
13 Reinforcement piece

The invention claimed is:

1. A bone-fixation anchor comprising:
   a first part made of a first material and having an opening shaped to correspond to a thread of a screw; and
   a second part made of a second material and configured to be expandable,
   wherein the second part extends from an end of the first part, and
   wherein the second material is rigid relative to the first material.

2. The bone-fixation anchor of claim 1, wherein the opening of the first part is a helical opening.

3. The bone-fixation anchor of claim 2, wherein the helical opening includes a width and length such that when a threaded screw is inserted into the first part, threads of the screw stand out of the helical opening.

4. The bone-fixation anchor of claim 1, wherein the first part includes an inner surface having a first diameter when no screw is disposed therein and a second diameter when a screw is disposed therein.

5. The bone-fixation anchor of claim 1, wherein the second part includes at least two anchor blades interconnected through a plurality of circumferential elastic rings such that the second part expands when a screw is inserted therein and contracts when the screw is removed.

6. The bone-fixation anchor of claim 1, wherein the first part has a first crosssectional shape and the second part has a second cross-sectional shape, the first cross-sectional shape being different from the second cross-sectional shape.

7. The bone-fixation anchor of claim 1, wherein the second part further comprises at least one longitudinal reinforcement piece.

8. The bone-fixation anchor of claim 1, wherein the first part further comprises a protrusion located at an end of the first part remote from the second part, the protrusion configured to engage with bone.

9. A bone-fixation anchor, comprising:
   a first part including an interior layer and an exterior layer, the interior layer constructed of a softer material than the exterior layer; and
   a second part configured to be deformable,
   wherein interior layer includes an inner diameter configured to change in size as a function of a diameter of a screw inserted therein.

10. The bone-fixation anchor of claim 9, wherein the interior layer of the first part is made of a material such that a screw having a diameter larger than an inner diameter of the interior layer causes the inner diameter to increase upon insertion of the screw.

11. The bone-fixation anchor of claim 10, wherein the exterior layer of the first part is made of material such that inflation of the exterior layer is prevented when radial loads bear on the exterior layer from within the anchor.

12. The bone-fixation anchor of claim 10, wherein the interior layer includes an inward facing surface configured to contact screws of differing diameters inserted into the anchor.

13. The bone-fixation anchor of claim 9, wherein the interior layer has a young's modulus less than 10 GPa.

14. The bone-fixation anchor of claim 13, wherein the interior layer is silicon or polyethylene and the exterior layer is a polymer.

15. The bone-fixation anchor of claim 9, wherein the second part includes at least two anchor blades interconnected through a plurality of circumferential elastic rings such that the second part expands when a screw is inserted therein and contracts when the screw is removed.

16. A bone-fixation anchor, comprising:
 a first part including an inner portion and an outer portion, the outer portion movable relative to the inner portion; and
 a second part extending from the first part,
 wherein movement of the outer portion relative to the inner portion causes the second part to deform,
 wherein the inner portion of the first part and the second part are monolithic.

17. The bone-fixation anchor of claim 16, wherein the outer portion is incrementally adjustable relative to the inner portion.

18. The bone-fixation anchor of claim 16, wherein the outer portion of the first part is configured to advance toward the second part as a screw disposed within the anchor is withdrawn.

19. The bone-fixation anchor of claim 16, wherein the second part includes at least two blades configured to move toward one another when the outer portion moves toward the second part.

\* \* \* \* \*